United States Patent [19]

Matsubara et al.

[11] 4,283,398

[45] Aug. 11, 1981

[54] CEPHALOSPORINS

[75] Inventors: Akira Matsubara, Yokohama; Hideaki Sakai, Fujisawa; Toshio Suganuma, Mobara; Nobuyuki Fukazawa; Takuo Nakano, both of Yokohama, all of Japan

[73] Assignee: Mitsui Toatsu Chemicals, Inc., Tokyo, Japan

[21] Appl. No.: 97,146

[22] Filed: Nov. 26, 1979

[30] Foreign Application Priority Data

Nov. 28, 1978 [JP] Japan .................. 53-146053

[51] Int. Cl.³ .......................... C07D 501/36
[52] U.S. Cl. ...................... 424/246; 544/27
[58] Field of Search ................. 544/27, 21; 424/246

[56] References Cited

U.S. PATENT DOCUMENTS

| 4,015,000 | 3/1977 | Kocsis et al. | 544/27 |
| 4,061,748 | 12/1977 | Yamara et al. | 544/27 |
| 4,117,126 | 9/1978 | Yamara et al. | 544/27 |
| 4,156,724 | 5/1979 | Yamara et al. | 544/27 |
| 4,160,087 | 7/1979 | Yamara et al. | 544/27 |
| 4,165,373 | 8/1979 | Yamara et al. | 544/27 |

FOREIGN PATENT DOCUMENTS 54-119484 9/1979 Japan .

OTHER PUBLICATIONS

Nishida et al., Jour. of Antibiotics, vol. XXIII, No. 3, pp. 137-148 (1970).
Rolinson et al., Antimicrobial Agents and Chemotherapy, pp. 609-613 (1967).
Williams et al., Antimicrobial Agents and Chemotherapy, pp. 388-391 (1968).

Primary Examiner—Nicholas S. Rizzo
Attorney, Agent, or Firm—Fisher, Christen & Sabol

[57] ABSTRACT

A cephalosporanic acid of the general formula

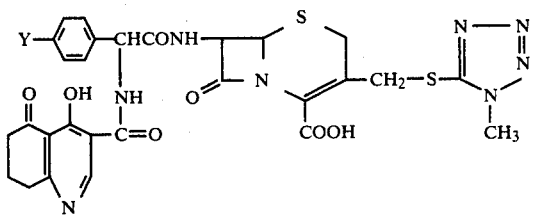

wherein Y represents a hydrogen atom or a hydroxyl group, and the biologically acceptable salt and ester thereof.

8 Claims, No Drawings

CEPHALOSPORINS

This invention relates to novel cephalosporins, and more specifically, to cephalosporanic acids of the general formula

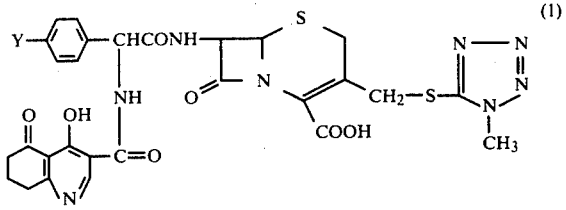

wherein Y represents a hydrogen atom or a hydroxyl group, and the biologically acceptable salts or esters thereof.

In recent years, the number of infectious diseases caused by *Pseudomonas aeruginosa* has increased, and these infectious diseases are often difficult to cure. It is desired therefore to develop drugs which are effective for infectious diseases caused by *Pseudomonas aeruginosa* with reduced side-effects.

It is known from J. Antibiotics, 23 (3), 137 (1970), etc. that cephalosporin-type compounds such as cephazoline (for example, sodium cephazoline, sodium 7-[1-(1H)-tetrazoylacetamido]-3-[2-(5-methyl-1,3,4-thiadiazoyl)-thiomethyl]-$\Delta^3$, cephem-4-carboxylate; to be abbreviated CEZ) are effective as therapeutic agents for infections caused by Gram-positive or Gram-negative bacteria. These agents, however, are ineffective for infections caused by *Pseudomonas aeruginosa*, and no cephalosporin-type compound effective against *Pseudomonas aeruginosa* has been marketed. It is known, on the other hand, from "Antimicrobial Agents and Chemotherapy"-1967, 609 (1968) and ibid.-1968, 388 (1968) that carbenicillin (for example, sodium carbenicillin, disodium-α-carboxybenzyl penicillin, to be abbreviated CB-PC) has been used mainly for the treatment of infections caused by *Pseudomonas aeruginosa*. Since, however, this drug has a low activity on *Pseudomonas aeruginosa*, it must be administered in high doses. Moreover, it is ineffective for *Pseudomonas aeruginosa*-induced infections of difficultly curable nature.

It is an object of this invention therefore to provide a drug which has a strong antibacterial activity on Gram-positive and Gram-negative bacteria and a high activity on *Pseudomonas aeruginosa*.

As a drug meeting this object, the present invention provides the cephalosporanic acids of general formula (1), and the biologically acceptable salts and esters thereof.

Examples of the cephalosporanic acids of general formula (1) include 7-[D-(—)-α-(4-hydroxy-5-oxo-5,6,7,8-tetrahydroquinoline-3-carboxamido)-phenylacetamido]-3[[(1-methyl-1H-tetrazol-5yl)thio]-methyl]-$\Delta^3$-cephem-4-carboxylic acid, and 7-[D-(—)-α-(4-hydroxy-5-oxo-5,6,7,8-tetrahydroquinoline-3-carboxamido)-α-(4-hydroxyphenyl)acetamido]-[[(1-methyl-1H-tetrazol-5-yl)thio]methyl]-$\Delta^3$-cephem-4-carboxylic acid.

The biologically acceptable salts of the cephalosporanic acids of general formula (1) include alkali metal salts such as lithium, sodium or potassium salts; alkaline earth metal salts such as calcium or magnesium salts; basic amino acid salts such as lysine, arginine or ornithine salts; and ordinary organic base salts such as triethylamine, benzylamine or procaine salts.

The biologically acceptable esters of the cephalosporanic acids of general formula (1) contain ordinary ester groups known in the field of cephalosporins. The ester groups may, for example, be those expressed by the following general formula

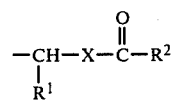

wherein $R^1$ represents a hydrogen atom or a lower alkyl group having 1 to 5 carbon atoms, $R^2$ represents a lower alkyl group having 1 to 5 carbon atoms, and X represents an oxygen or sulfur atom.

The cephalosporin compounds of this invention have a broad range of antibacterial spectrum and a strong antibacterial activity against Gram-negative bacteria, especially bacteria of the genus Pseudomonas. Hence, they are useful as therapeutic agents for infections by these bacteria.

The cephalosporin in accordance with this invention can be produced by reacting a compound of the general formula

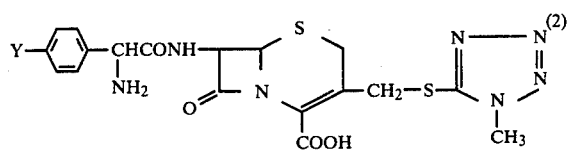

wherein Y is as defined in general formula (1), or a salt or reactive derivative thereof, with a reactive derivative of 4-hydroxy-5-oxo-5,6,7,8-tetrahydroquinoline-3-carboxylic acid of the general formula

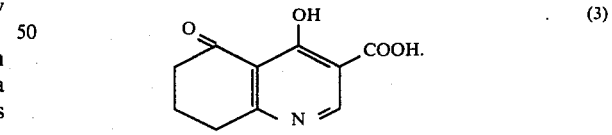

The cephalosporin of the invention can also be produced by reacting a compound of the general formula

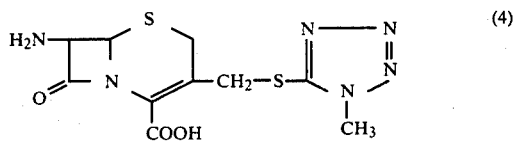

or a salt or reactive derivative thereof, with a reactive derivative of a carboxylic acid of the general formula

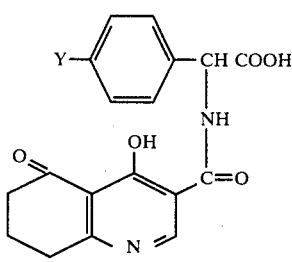

wherein Y is as defined in general formula (1).

The compounds of general formula (2) and formula (4) are known in the art. 4-Hydroxy-5-oxo-5,6,7,8-tetrahydroquinoline-3-carboxylic acid of general formula (3) is a novel compound, and can be prepared, for example, by preparing diethyl N-(3-oxo-1-cyclohexene-1-yl)aminomethylenemalonate from 3-amino-2-cyclohexenone and dimethyl ethoxy-methylenemalonic acid, heating this product to cyclize it to ethyl 4-hydroxy-5-oxo-5,6,7,8-tetrahydroquinoline-3-carboxylate, and hydrolyzing this product. Examples of the reactive derivatives of 4-hydroxy-5-oxo-5,6,7,8-tetrahydroquinoline-3-carboxylic acid of formula (3) include its acid halides, mixed acid anhydrides, and active esters.

The reaction of the compound of formula (2) or its salt or ester with the reactive derivative of the quinoline carboxylic acid of formula (3) is carried out usually in a reaction solvent. Suitable reaction solvents, include, for example, tetrahydrofuran, methylene chloride, chloroform, dioxane, acetic acid esters, and dimethylformamide.

The reaction of the cephalosporanic acid of formula (4) or its salt or reactive derivative with the reactive derivative of the carboxylic acid of formula (5) is carried out in an aqueous solvent or a non-aqueous organic solvent. The carboxylic acid of general formula (5) can be prepared by reacting D-(−)-phenylglycine or D-(−)-4-hydroxyphenylglycine with the reactive derivative of the quinoline carboxylic acid of formula (3). Suitable reactive derivatives of the carboxylic acid of general formula (5) include acid halides, mixed anhydrides, and active esters.

The following Synthesis Examples especifically illustrate the process for producing cephalosporins in accordance with this invention.

SYNTHESIS EXAMPLE 1

Synthesis of 7-[D-(−)-α-(4-hydroxy-5-oxo-5,6,7,8-tetrahydroquinoline-3-carboxamide)phenylacetamido)-3-[[(1-methyl-1H-tetrazol-5-yl)thio]methyl]-Δ³-cephem-4-carboxylic acid:

To 20 ml of methylene chloride were added 0.60 g of 4-hydroxy-5-oxo-5,6,7,8-tetrahydroquinoline-3-carboxylic acid and 0.65 g of triethylamine. The mixture was cooled to −15° C. to −10° C., and a solution of 0.69 g of ethyl chloroformate in 5 ml of methylene chloride was added dropwise. The mixture was stirred at −15° C. to −10° C. for 30 minutes, and a solution of 1.6 g of 7-[D-(−)-α-amino-phenylacetamido]-3-[[(1-methyl-1H-tetrazol-5-yl)thio]methyl]-Δ³-cephem-4-carboxylic acid in 20 ml of methylene chloride and 0.88 g of triethylamine. The reaction was carried out at −15° C. to 0° C. for 1.5 hours, and then the solvent was distilled off. Water (50 ml) was added, and the pH of the mixture was adjusted to 2 with 40% phosphoric acid. The crystals which precipitated were collected by filtration. Then, the crystals were purified by using a column filled with silica gel to afford 0.12 g of the captioned product.

The infrared absorption spectrum of this product, determined by the KBr tablet method, had maximum absorptions at 1790, 1690 (with shoulder), 1620, 1540, 1505, 1410, 1365, 1185, 820, and 705 cm⁻¹.

SYNTHESIS EXAMPLE 2

Synthesis of 7-[D-(−)-α-(4-hydroxy-5-oxo-5,6,7,8-tetrahydroquinoline-3-carboxamide)-α-(4-hydroxyphenyl)acetamido]-3-[[(1-methyl-1H-tetrazol-5-yl)thio]methyl]-Δ³-cephem-4-carboxylic acid:

In 200 ml of dimethylformamide were suspended 10.0 g of 4-hydroxy-5-oxo-5,6,7,8-tetrahydroquinoline-3-carboxylic acid and 6.12 g of N-hydroxysuccinimide. The suspension was cooled to −10° C., and a solution of 6.9 g of thionyl chloride in 50 ml of dimethylformamide was added dropwise. The mixture was stirred at 0° at 50° C. for 24 hours, and then at room temperature for 3 hours, and cooled to below 10° C. Pyridine (10.1 g) was added dropwise, and the mixture was stirred at room temperature for 4 hours, followed by cooling. The crystals which precipitated were collected by filtration to afford 9.74 g of yellow crystals having a melting point of 252° to 255° C. (decomp.; uncorrected). In 50 ml of dimethylformamide were suspended 3.51 g of the resulting yellow crystals and 5.50 g of 7-[D-(−)-α-amino-α-(4-hydroxyphenyl)acetamido]-3-[[(1-methyl-1H-tetrazol-5-yl)thio]methyl]-Δ³-cephem -4-carboxylic acid. The suspension was cooled to −2° C. to 0° C., and a solution of 2.12 g of triethylamine in 5 ml dimethylformamide was added dropwise. The mixture was stirred at −2° C. to 0° C. for 30 minutes, and the reaction mixture was poured into 500 ml of acetone. Ether (500 ml) was added, and the crystals that precipitated were collected by filtration. The crystals were purified by using a column packed with silica gel to afford 2.0 g of the captioned product.

The infrared absorption spectrum of this product had maximum absorptions at 1790, 1690, 1620, 1520, 1500, 1360, 1240, 1190 and 820 cm⁻¹.

The antibacterial activities of the cephalosporins of this invention were measured using the sodium salts of the compounds obtained in Synthesis Examples 1 and 2. The procedure and the results are shown in Referential Example 1.

REFERENTIAL EXAMPLE 1

Carbenicillin sodium salt (CB-PC) and cephazoline sodium salt (CEZ) were used as controls.

The antibacterial activities of the test compounds against various Gram-positive and Gram-negative bacteria were determined in a customary manner by the minimum growth inhibitory concentration method (MIC method).

The experimental procedure was as follows:

A commercially available heart infusion agar medium (to be abbreviated HIA medium) was used as an assay medium, and a commercially available trypto-soy bouillon medium (to be abbreviated TSB) was used as a medium for the growth of test bacterial strains.

The test compound was diluted with the melted HIA medium to 100 μg/ml as a maximum concentration, and then serially diluted double. The dilutions were poured into sterilized Petri dishes respectively and allowed to cool and solidify to prepare plates containing the test compound.

The test bacterial strain was cultivated at 37° C. for 18 to 24 hours in the TSB medium. The culture broth was diluted to 50 to 500 times with a freshly prepared TSB culture medium, and one platinum loopful of the dilution was inoculated in each of the plates containing the test compound. The plate was incubated at 37° C. for 18 hours, and the state of growth of the strain on the plate was observed, and the minimum growth inhibitory concentration (MIC) of the test compound was determined. The results are shown in Table 1.

It is seen from Table 1 that the compounds of this invention have a broad range of antibacterial spectrum, and their antibacterial activities are of high level. In particular, they have much better antibacterial activity against *Pseudomonas aeruginosa* strains than CB-PC and CEZ, and are useful as anti-*Pseudomonas aeruginosa* drugs.

TABLE 1

| Test bacteria | Test compounds Synthesis Example 1 | Synthesis Example 2 | CB-PC | CEZ |
|---|---|---|---|---|
| | Minimum growth inhibitory concentration ($\mu$g/m.) | | | |
| *Staphylococcus aureus* (FDA 209P) | 1.56 | 1.56 | 1.56 | 0.20 |
| *Staphylococcus aureus* (Y-8) | 3.13 | 3.13 | 12.5 | 0.78 |
| *Streptococcus faecalis* (Hoshi) | 25 | 25 | 50 | 25 |
| *Bacillus cereus* (IAM 1792) | 25 | 12.5 | 100 | 100 |
| *Escherichia coli* (K-12) | 0.78 | 0.39 | 6.25 | 3.13 |
| *Escherichia coli* (NIHJ) | 0.78 | 0.78 | 6.25 | 3.13 |
| *Escherichia coli* (26R03) | 1.56 | 0.78 | 3.13 | 50 |
| *Escherichia coli* (14H114) | 6.25 | 6.25 | >100 | 6.25 |
| *Klebsiella pneumoniae* (ATCC 10031) | 0.20 | 0.39 | >100 | 1.56 |
| *Klebsiella pneumoniae* (Horino) | 1.56 | 0.78 | 100 | 3.13 |
| *Klebsiella pneumoniae* (B-172) | 0.78 | 0.78 | 25 | 3.13 |
| *Klebsiella pneumonia* (F-5089) | — | — | 50 | 3.13 |
| *Shigella flexneri* (K-A) | 0.20 | 0.10 | 1.56 | 1.56 |
| *Salmonella enteritidis* (KB-21) | 0.78 | 0.39 | 1.56 | 1.56 |
| *Proteus vulgaris* (OX-19) | 1.56 | 0.78 | 6.25 | 1.56 |
| *Proteus rettgeri* (T-2) | 1.56 | 1.56 | 3.13 | 12.5 |
| *Proteus morganii* (C-39) | 3.13 | 3.13 | 6.25 | >100 |
| *Pseudomonas aeruginosa* (IFO-3901) | 12.5 | 12.5 | 100 | >100 |
| *Pseudomonas aeruginosa* (S-1) | 1.56 | 1.56 | 25 | >100 |
| *Pseudomonas aeruginosa* (395) | 3.13 | 1.56 | 25 | >100 |
| *Pseudomonas aeruginosa* (NCTC 7244) | 12.5 | 6.25 | 100 | >100 |
| *Pseudomonas aeruginosa* (ATCC 10145) | 12.5 | 12.5 | >100 | >100 |
| *Pseudomonas aeruginosa* (718) | 12.5 | 12.5 | >100 | >100 |
| *Pseudomonas aeruginosa* (F1629) | 6.25 | 3.13 | >100 | >100 |
| *Enterobacter cloacae* (D-49) | 6.25 | 3.13 | >100 | >100 |
| *Enterobacter aerogenes* (IFO 3320) | 0.20 | 0.20 | 1.56 | 3.13 |
| *Citrobacter freundii* (F-34) | 0.78 | 0.39 | 3.13 | 50 |
| *Serratia marcescens* (S-33) | 3.13 | 3.13 | 6.25 | >100 |
| *Pseudomonas Maltophilia* (F-6257) | 3.13 | 6.25 | 25 | >100 |

Referential Example 2 shows that the compounds of this invention have superior antibacterial activity against *Pseudomonas aeruginosa* strains.

REFERENTIAL EXAMPLE 2

The compounds obtained in Synthesis Examples 1 and 2 were tested in the following manner.

A suspension of *Pseudomonas aeruginosa* (NCTC 7244) cultivated at 37° C. for 18 hours in a heart infusion broth medium (HIB medium) in a final amount of $10^5$, $10^6$ and $10^7$ cells/ml in an HIB medium containing each of the test compounds which was obtained in the same way as in Referential Example 1 except that the maximum concentration of the test compound was 200 $\mu$g/ml. The bacterial strain was cultivated at 37° C. for 18 hours, and the turbidity of the culture broth was evaluated with the naked eye. The minimum concentration of the test compound at which no turbidity was noted was defined as MIC.

After the determination of MIC, one platinum loopful of each of the culture broths in various concentrations was taken out from the test tubes, and inoculated in a separately provided plate of an HIA medium not containing the test compound, and incubated at 37° C. for 18 hours. The growth of the bacterial strain was evaluated. The minimum concentration of the test compound among those plates which did not show growth of the bacterial strain was defined as the minimum bactericidal concentration (MBC) of the test compound.

The results are shown in Table 2 from which it is seen that the bactericidal activity of the compounds of this invention is strong.

TABLE 2

| | | Amount of the bacterial strain inoculated (cells/ml) | | |
|---|---|---|---|---|
| | | $10^5$ | $10^6$ | $10^7$ |
| Compound of synthesis Example 1 | MIC | 12.5 | 12.5 | 25 |
| | MBC | 12.5 | 12.5 | >200 |
| Compound of synthesis Example 2 | MIC | 6.25 | 6.25 | 12.5 |
| | MBC | 6.25 | 12.5 | >200 |
| CB-PC | MIC | 50 | 100 | 200 |
| | MBC | 100 | 100 | >200 |
| CEZ | MIC | >200 | >200 | >200 |
| | MBC | >200 | >200 | >200 |

The following Experimental Examples illustrate the concentrations of the compounds of this invention in blood in rats and their acute toxicities in mice.

EXPERIMENTAL EXAMPLE 1

The compounds of this invention prepared in synthesis Examples 1 and 2 were each administered intramuscularly to rats, and the concentrations of the compounds in the blood were determined.

Each of the test compounds was intramuscularly injected into the femoral part of rats in a customary manner in a dose of 20 mg/kg for each rat. The blood was drawn by incising the cervical artery and vein at the end of 15 minutes, 30 minutes, 60 minutes, 120 minutes, and 240 minutes after the injection. The separated sera were used for the measurement of the blood level of the test compound. The concentrations of the test compounds in the sera were determined by a thin-layer cup method using *Micrococcus luteus* ATCC 9341 as an assay microorganism.

The results are shown in Table 3.

It is seen from the results that the state of the blood levels of the compounds of this invention in rats is of the high level-retaining type, and the compounds of this invention are useful for the treatment of infections.

TABLE 3

| Test compound | Dose (mg/kg; i.m.) | Blood level after administration (average value ± standard deviation, μg/ml) | | | | |
|---|---|---|---|---|---|---|
| | | 15 minutes | 30 minutes | 60 minutes | 120 minutes | 240 minutes |
| Synthesis Example 1 | 20 | 12.1 ± 3.6 | 10.5 ± 2.2 | 9.1 ± 3.2 | 4.8 ± 2.1 | — |
| Synthesis Example 2 | 20 | 20.0 ± 1.4 | 14.4 ± 2.5 | 8.0 ± 4.0 | 3.2 ± 1.2 | — |

EXPERIMENTAL EXAMPLE 2

Each of the compounds of this invention obtained in synthesis Examples 1 to 4 was intravenously administered to ICR male mice having a body weight of 25 g of groups each consisting of 10 mice, and the 50% lethal dose (LD$_{50}$) was estimated. Each of the compounds was administered intravenously to the tail of each mouse in a customary manner in a dose of 500 mg/kg and 1000 mg/kg, and over two weeks from then, the states of the mice were observed. It was consequently estimated that the LD$_{50}$ values of each of these compounds was at least 1000 mg/kg.

As is apparent from the foregoing description, the cephalosporins of this invention have very good antibacterial activity, and are useful as antibacterial agents. They can be used not only for the treatment and prevention of bacterial infections of mammals including humans and also as disinfectants. In administration to humans, the dose of the cephalosporin of this invention is 100 mg to 2000 mg, preferably 250 mg to 1000 mg, per administration. Desirably, it is administrated several times a day.

Pharmaceuticals containing the compound of this invention as an active ingredient may be in the form of solids such as tablets, capsules and powders or liquids such as injections or suspensions. Additives usually employed in the art, such as vehicles, stabilizers and wetting agents may be used.

What we claim is:

1. A cephalosporanic acid of the formula

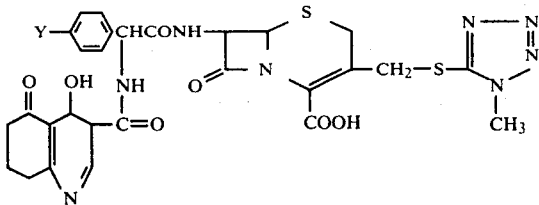

wherein Y represents a hydrogen atom or a hydroxyl group, and pharmaceutically acceptable salts and esters thereof.

2. The salt of claim 1 which is a salt of an alkali metal, an alkaline earth metal, a basic amino acid or an organic base.

3. The ester of claim 1 which has an ester group of the formula

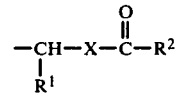

wherein R$^1$ represents a hydrogen atom or a lower alkyl group having 1 to 5 carbon atoms, R$^2$ represents a lower alkyl group having 1 to 5 carbon atoms, and X represents an oxygen or sulfur atom.

4. The compound of claim 1 wherein Y represents a hydrogen atom.

5. The compound of claim 1 wherein Y represents a hydroxyl group.

6. An antibacterial agent comprising a pharmaceutically effective amount of a cephalosporanic acid of the formula

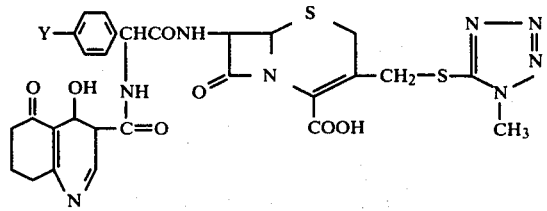

wherein Y represents a hydrogen atom or a hydroxyl group, or a pharmaceutically acceptable salt or ester thereof as an active ingredient, and a pharmaceutical vehicle.

7. The antibacterial agent of claim 6 wherein Y represents a hydrogen atom.

8. The antibacterial agent of claim 6 wherein Y represents a hydroxyl group.

* * * * *